US006348190B1

(12) United States Patent
Illes et al.

(10) Patent No.: US 6,348,190 B1
(45) Date of Patent: Feb. 19, 2002

(54) PHARMACEUTICAL COMPOSITIONS WITH ANTIMICROBIAL ACTIVITY

(75) Inventors: Janos Illes; Erzsebet Nesmelyi; Bela Stefko, all of Budapest; Kalman Burger, Szeged, all of (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 09/254,386

(22) PCT Filed: Sep. 11, 1997

(86) PCT No.: PCT/HU97/00052

§ 371 Date: Mar. 4, 1999

§ 102(e) Date: Mar. 4, 1999

(87) PCT Pub. No.: WO98/10773

PCT Pub. Date: Mar. 19, 1998

(30) Foreign Application Priority Data

Sep. 12, 1996 (HU) .............................................. 9602498

(51) Int. Cl.$^7$ ................................................. A61K 31/74
(52) U.S. Cl. ........................ 424/78.04; 514/54; 514/912
(58) Field of Search ........................ 514/54; 424/78.04, 424/912

(56) References Cited

U.S. PATENT DOCUMENTS 4,623,539 A   11/1986   Tunc

OTHER PUBLICATIONS

JP 6048950; Antiulcer agents; Pub.: Feb. 22, 1994; Pat. Appl. 4–204079; Filed Jul. 30, 1992; Applicant: Taito, KK.

*Primary Examiner*—Zohreh Fay
(74) *Attorney, Agent, or Firm*—Herbert Dubno; Jonathan Myers

(57) ABSTRACT

The invention relates to pharmaceutical compositions of antimicrobial effect as well as a process for the preparation thereof. The pharmaceutical compositions of the invention comprise zinc or cobalt hyaluronate associate (complex) as active ingredient in admixture with a carrier and/or other additives commonly used in the pharmaceutical industry.

4 Claims, No Drawings

PHARMACEUTICAL COMPOSITIONS WITH ANTIMICROBIAL ACTIVITY

SPECIFICATION

Field of the Invention

The invention relates to pharmaceutical compositions of antimicrobial activity containing associates (complexes) of hyaluronic acid as well as a process for the preparation thereof.

The invention furthermore relates to the use of these hyaluronic acid associates (complexes) for the preparation of pharmaceutical compositions of antimicrobial activity and a method for the treatment of microbes-induced clinical pictures.

Now, it has been found that associates (complexes) of hyaluronic acid, i.e. zinc and cobalt hyaluronates showed antimicrobial activity and especially they have favorable antibacterial and fungicidal effects against aerobic and anaerobic microorganisms.

BACKGROUND OF THE INVENTION

Associates of deprotonated hyaluronic acid with 3d metal ions of 4th period of the Periodic Table such as zinc and cobalt hyaluronates with a curative effect especially on crural ulcer, decubitus or the like are discussed in the Hungarian patent specification No. 203,372.

The macromolecule known as hyaluronic acid usually occurring in the form of its sodium salt, is a compound known for more than 50 years. It had first been described by Meyer and al [J. Biol. Chem. 107, 629 (1934); J. Biol.Chem. 114, 689 (1939)]. Meyer isolated the hyaluronic acid under acidic conditions. However, the carboxyl groups are dissociated at a physiological pH value; and the name of the polysaccharide is sodium hyaluronate if the environmental cation is sodium. The structure determination was performed by Weissman et al [J. Am. Chem. Soc. 76, 1753 (1954)]. The determination of environmental cation is not always simple therefore, as proposed by Balázs (The Biology of Hyaluronan 1989, John Wiley and Sons, Ciba Foundation Symposium, p. 143), the general name of the polysaccharide (both hyaluronic acid and sodium hyaluronate) is hyaluronan.

Hyaluronic acid is a highly viscous native glucosaminoglycan containing alternating β1–4 glucosamine moieties; its molecular weight is between 50000 and several millions. Hyaluronic acide is found in the connective tissues of all mammals: it occurs in higher concentration in the skin, vitreous body of eye, synovial fluid, umbilical cord as well as cartilaginous tissue. The recovery of hyaluronic acid is an old task, the separation and use of an ultrapure hyaluronic acid are described e.g. in the U.S. Pat. Nos. 4,141,973 and 4,303,676 and in the European patent specification No. 0,144,019.

A number of references relating to the connection of hyaluronic acid with the wound-healing are found in the literature. According to Toole and Gross [B. P. Toole és Gross: "The extracellular matrix of the regenerating newt limb: synthesis and removal of hyaluronate prior to differentiation", Dev. Biol. 25, 55–57 (1971)], hyaluronic acid as the main constituent of the extracellular matrix is responsible for the migration of various cell types. The above authors stated by experimental investigations that, during the wound-healing, the local concentration of hyaluronic acid increased whereby the cellular reactions required to the tissue regeneration were stimulated. In addition to the above, other experimental results also confirm that hyaluronic acid regulates the wound-healing physiological cellular events by providing the optimum conditions for migration and proliferation of all cells sharing in the tissue regeneration.

Up to the last years, hyaluronic acid has been employed as sodium salt in the theraphy—mainly in the ophthalmology, dermatology, surgery, articular therapy—and cosmetics. The salts of hyaluronic acid formed with alkaline, alkaline earth, magnesium, aluminium, ammonium and substituted ammonium ions may serve as carriers for promoting the absorption of drugs (see the Belgian patent specification No. 904,547). Heavy metal salts of hyaluronic acid, among these the silver salt, are employed as fungicides whereas the gold salt is employed for the treatment of arthritis (see the patent specification No. WO 87/05517). However, it is known the severe adverse effects of silver and gold compounds, i.e. their effects on the immune system, haematopoietic organs and nervous system [M. Shinogi, S. Maeizumi: "Effect of preinduction of metallothionein on tissue distribution of silver and hepatic lipid peroxidation", Biol. Pharm Bull. (Japan) 16, 372–374 (1993); C. Masson et al: Rev. Med. Interne (France) 13, 225–232 (1992)].

SUMMARY OF THE INVENTION

We have surprisingly found, that hyaluronic acid associates, i.e. zinc and cobalt hyaluronates, which are useful for accelerating the epithelization of epithelium-deficient body surfaces, for healing crural ulcer as well as decubital ulcer, possess significant antimicrobial, more particularly antibacterial and fungicidal effects; in addition, within the antibacterial activity they proved to be active also against *Helicobacter pylory* bacteria recently considered to be responsible for the development of gastric and duodenal ulcers.

The antibacterial effects of hyaluronic acid associates are thought to be surprising since it can be supposed that the wound-healing epithelization-promoting effects of hyaluronic acid associates known until now are based on the above-discussed body-friendly behavior of hyaluronic acid during the wound-healing but the antimicrobial effect of hyaluronic acid associates cannot be concluded therefrom.

According to our investigations, zinc and cobalt associates of hyaluronic acid proved to be very active against either aerobic or anaerobic bacteria such as *Staphylococcus aureus*, Streptococcus sp., *Pseudomonas aeruginosa*, Salmonella sp., *E. coli* and *Helicobacter pylon.*

Since *Staphytococcus aureus* and *Pseudomonas aeruginosa* are the two types of bacteria that are implicated in eye infections, the fact, that the hyaluronate complexes are effective against both of these microorganisms is very important and using the hyaluronic acid associates in the ophthalmology seems especially promising.

The intraocular use of sodium hyaluronate in the ophthalmology is known. Since 1980 it has been widely used in the case of cataracta surgery, artificial lens implantations, keratoplasty. When administered into the anterior chamber, it inhibits the collapse thereof during operation and protects the sensitive tissues and cells. After the surgical intervention, sodium hyaluronate is washed out from the eye to avoid the increase of ocular pressure occurring in some cases.

Sodium hyaluronate is used also in the treatment of the "dry eye" syndrome [F. M. Polack et al: "The treatment of dry eyes with Na-hyaluronate" Cornea, 133–136 (1982)].

The topical antibacterial treatment of eye infections is an other important field of utilization of associates of the present invention.

Due to their antibacterial effect, zinc and cobalt hyaluronate associates seem to be particularly useful in the ophthalmological therapeutics; mainly zinc hyaluronate appears to be very promising in this area. In addition to its lubricant effect, zinc hyaluronate can advantageously be employed as a topical antibacterial agent in the ophthalmology; but it can be used also in the ocular surgery as a competitor of sodium hyaluronate widely used intraocularly since 1980, due to its antibacterial effect, to overcome the occurring mild inflammatory reactions [K. L. Goa et al: "Hyaluronic Acid, a Review of its Pharmacology and Use", Drugs 47, 536–566 (1994)] and to reduce the risk of infection during the operation. The role of zinc as an essential trace element in the eye has long. been recognized [D. A. Newsome, R. J. Rothman: "Zinc uptake in vitro by human retinal pigment epithelium", Invest. Ophthalmol. Vis. Sci. 28, 795–799 (1987)]. Zinc hyaluronate has the particular advantage that, by using it, the decrease of zinc possibly occurring in eye operations can be avoided. Namely, hyaluronic acid as a polyanion can take away cations by the washing-out after operation. It cannot be excluded that zinc being bound also through a coordinative bond to hyaluronate, may be decreased in the eye. This phenomenon can be eliminated by using zinc hyaluronate.

It is known, that bacterial contamination of the eye is a serious health problem. The most frequent contaminant is the Staphylococcus group. Less frequently the contaminant is *Pseudomonas aeruginosa* which is also very dangerous to the eye. Infection of the eye with these bacteria can result in complete blindness over a 24 to 48 hour period. The infections of eye are frequently caused by contaminated ophthalmological solutions (eye drops, solutions for the storage of contact lenses or the like). Such contaminated ophthalmological solutions occur in consulting rooms, clinics and very frequently in the home use. The contaminating microbe most frequently belongs to the Staphylococcus group; however, the less frequent but more dangerous *Pseudomonas aeruginosa* is also capable of rapid growth in ophthalmological solutions (Remington's Ophthalmic Preservatives, Chapter 86, 1588). Thus, the use of zinc and cobalt hyaluronate associates in the ophthalmology may be very important by their strong activity against both species of the above microorganisms.

The antimicrobial effect of the compounds was verified by microbiological investigations. Zinc hyaluronate and cobalt hyaluronate solutions according to the Hungarian patent specification No. 203,372 were used for these examinations whereas sodium hyaluronate solutions served as reference solutions.

The following Example 1 shows preparation of a 0.5% zinc hyaluronate solution. Unless otherwise noted the percentages hereinafter are always weight/volume values.

Solutions of 0.1 or 0.2% concentration respectively were obtained by diluting 0.5% zinc hyaluronate solution with distilled water of quality according to the example.

EXAMPLE 1

Preparation of 100 ml of 0.5% Zinc Hyaluronate Solution

The characteristics of sodium hyaluronate used for the preparation of the solution are as follows:

| Molecular weight: | 1 000 000 dalton |
|---|---|
| Protein content: | 0.045% |
| UV absorption: | 1% |
| A | : 0.085 |
| | 257 nm |
| | 1% |
| A | : 0.050 |
| | 280 nm |
| | C→O |
| Viscosity: | η = 17.25 dl/g |
| | 25 °C. |
| Hyaluronic acid content: | 99.3% |

After weighing 0.50 g of sodium hyaluronate in a 100 ml flask, 12.50 ml of zinc chloride solution of 0.10 mol/liter concentration prepared with twice distilled water (water for injection use, pyrogen-free, sterile) are added, then the volume is filled up to 50 ml with twice distilled water. It is allowed to swell overnight, then dissolved by shaking and filled up with twice distilled water. After filtering the solution through a membrane filter of 0.45 μm pore size, a solution containing 0.50% of zinc hyaluronate is obtained.

EXAMPLE 2

Preparation of 100 ml of 0.5% Sodium Hyaluronate Solution 0.50 g of sodium hyaluronate used in Example 1 is dissolved in 100 ml of twice distilled water (water for injection use, pyrogen-free, sterile) as previously described to obtain 0.5% sodium hyaluronate solution. Solutions of 0.1 or 0.2%, respectively are prepared by diluting the 0.5% solution with distilled water of the above quality.

First Series of Experiments

Zinc and sodium hyaluronate solutions of 0.2% (obtained by diluting solutions of 0.5% prepared according to Examples 1 and 2) were artificially infected by the identical germ count of various test organisms and the changing of the number of germs was taken against time. The number of germs was determined in a point of time by plating method. The evaluation was visually carried out at moulds and by using an automated colony counter at bacteria and fungi.

Medium applied: Soya-casein agar (Caso-agar /Merck/).

Microorganisms registered in National Strain Collection of National

Institute of Public Health (HNCMB) were employed as test organisms.

Microorganisms applied:

*Staphylococcus aureus,*

Streptococcus sp.,

*Escherichia coli,*

Salmonella sp.,

*Candida albicans,*

*Aspergillus niger*

Starting number of test organisms: Σ10⁶/ml

Number of parallel experiments: 3

The solutions applied:

1—Aqueous solution of zinc hyaluronate of 0.2%;

2—Aqueous solution of sodium hyaluronate of 0.2%.

The results are shown in Tables 1 and 2.

TABLE 1

The effect of aqueous solution of zinc hyaluronate of 0.2% against various test organisms
(given in test organism number per milliliter).

| Test organism | Time of sampling | | | | | | | |
|---|---|---|---|---|---|---|---|---|
| | 0 hr | 1 hr | 2 hrs | 3 hrs | 4 hrs | 5 hrs | 6 hrs | 24 hrs |
| Staphylococcus aureus | $4.80 \times 10^5$ | $4.75 \times 10^5$ | $4.50 \times 10^5$ | $3.60 \times 10^5$ | $1.00 \times 10^4$ | $8.00 \times 10^3$ | $4.50 \times 10^3$ | $1.00 \times 10^2$ |
| Streptococcus sp | $5.10 \times 10^5$ | $4.00 \times 10^5$ | $3.60 \times 10^4$ | $2.80 \times 10^4$ | $1.50 \times 10^3$ | $1.00 \times 0^3$ | $5.00 \times 10^2$ | <100 |
| Escherichia coli | $5.40 \times 10^5$ | $5.00 \times 10^5$ | $8.80 \times 10^4$ | $4.20 \times 10^4$ | $3.80 \times 10^4$ | $3.00 \times 10^4$ | $2.50 \times 10^4$ | $2.00 \times 10^3$ |
| Salmonella sp | $5.10 \times 10^5$ | $4.40 \times 10^5$ | $3.50 \times 10^4$ | $8.00 \times 10^3$ | $5.00 \times 10^3$ | $4.00 \times 10^3$ | $2.40 \times 10^3$ | 0 |
| Candida albicans | $5.20 \times 10^5$ | $4.80 \times 10^5$ | $4.00 \times 10^5$ | $9.00 \times 10^4$ | $5.00 \times 10^4$ | $4.20 \times 10^4$ | $3.60 \times 10^4$ | $1.60 \times 10^2$ |
| Aspergillus niger | $4.20 \times 10^5$ | $3.40 \times 10^4$ | $3.80 \times 10^4$ | $3.60 \times 10^4$ | $2.80 \times 10^4$ | $2.60 \times 10^4$ | $1.00 \times 10^4$ | $4.00 \times 10^3$ |

TABLE 2

The effect of aqueous solution of sodium hyaluronate of 0.2% against various test organisms
(given in test organism number per milliliter).

| Test organisms | 0 hr | 1 hr | 2 hrs | 3 hrs | 4 hrs | 5 hrs | 6 hrs | 24 hrs |
|---|---|---|---|---|---|---|---|---|
| Staphylococcus aureus | $5.00 \times 10^5$ | $5.10 \times 10^5$ | $4.90 \times 10^5$ | $5.00 \times 10^5$ | $4.80 \times 10^5$ | $4.85 \times 10^5$ | $4.50 \times 10^5$ | $4.20 \times 10^5$ |
| Streptococcus sp | $4.40 \times 10^5$ | $4.20 \times 10^5$ | $4.25 \times 10^5$ | $4.20 \times 10^5$ | $4.10 \times 10^5$ | $4.10 \times 10^5$ | $4.00 \times 10^5$ | $3.80 \times 10^5$ |
| Escherichia coli | $5.20 \times 10^5$ | $5.00 \times 10^5$ | $5.10 \times 10^5$ | $5.00 \times 10^5$ | $4.90 \times 10^5$ | $4.95 \times 10^5$ | $4.90 \times 10^5$ | $4.80 \times 10^5$ |
| Salmonella sp | $5.10 \times 10^5$ | $5.00 \times 10^5$ | $4.90 \times 10^5$ | $4.90 \times 10^5$ | $4.80 \times 10^5$ | $4.70 \times 10^5$ | $4.70 \times 10^5$ | $4.20 \times 10^5$ |
| Candida albicans | $4.20 \times 10^5$ | $4.00 \times 10^5$ | $4.10 \times 10^5$ | $4.10 \times 10^5$ | $4.20 \times 10^5$ | $4.50 \times 10^5$ | $4.50 \times 10^5$ | $5.00 \times 10^5$ |
| Aspergillus niger | $4.00 \times 10^5$ | $3.80 \times 10^5$ | $3.80 \times 10^5$ | $3.90 \times 10^5$ | $3.90 \times 10^5$ | $4.00 \times 10^5$ | $4.20 \times 10^5$ | $6.00 \times 10^5$ |

It can be seen from the above results summarized in Tables 1 and 2 that an essential difference appeared in the antimicrobial effects after 24 hours. The 0.2% zinc hyaluronate solution induced a reduction by several orders on the majority of investigated test organisms whereas the number of test organisms was not significantly changed in sodium hyaluronate solution.

Second Series of Experiments

In order to prove the antimicrobial effect of zinc hyaluronate, the experiments were further extended to solutions of other than 0.2% concentration together with various prolongations of the test time. The effects of 0.1% zinc hyaluronate and sodium hyaluronate solutions, respectively on three distinguished test organisms are illustrated in Table 3.

TABLE 3

| | Staphylococcus aureus Test-organism/ml | | Salmonella sp Test-organism/ml | | Pseudomonas aeruginosa Test-organism/ml |
|---|---|---|---|---|---|
| Time | Zn-hy | Na-hy | Zn-hy | Na-hy | Zn-hy |
| 0 hr | $4.2 \times 10^6$ | $1.3 \times 10^6$ | $2.0 \times 10^6$ | $8.0 \times 10^6$ | $2.1 \times 10^5$ |
| 24 hrs | $4.6 \times 10^6$ | $4.1 \times 10^6$ | $1.1 \times 10^6$ | $8.1 \times 10^6$ | $2.4 \times 10^4$ |
| 48 hrs | 0 | $6.2 \times 10^6$ | 0 | $1.2 \times 10^6$ | $3.0 \times 10^3$ |
| 72 hrs | 0 | $8.4 \times 10^6$ | 0 | $1.8 \times 10^6$ | <100 |
| 96 hrs | 0 | | 0 | | <100 |
| 168 hrs | 0 | | 0 | | 0 |

It can be seen that in the experiments with zinc hyaluronate, the counts of Staphylococcus and Salmonella test organisms were reduced to zero practically within 48 hours; whereas the results of investigations with sodium hyaluronate remained practically within the same order. A slower onset of effect was observed on *Pseudomonas aeruginosa* where a significant decrease appeared only from the second day.

Third Series of Experiments

Due to the ophthalmological importance of *Pseudomonas aeruginosa*, the effects of zinc hyaluronate solutions of various concentrations on *Pseudomonas aeruginosa* were studied in comparison to sodium hyaluronate solutions of the same concentrations. The results are summarized in Tables 4 and 5.

TABLE 4

Effect of zinc hyaluronate on *Pseudomonas aeruginosa*

| | Zn-hyaluronate solutions | | |
|---|---|---|---|
| Time | 0.1% | 0.2% | 0.5% |
| | Test-organism /ml | | |
| 0 hr | $5.5 \times 10^5$ | $8.0 \times 10^5$ | $1.0 \times 10^6$ |
| 24 hrs | $5.0 \times 10^5$ | $5.5 \times 10^5$ | $6.0 \times 10^5$ |
| 48 hrs | $2.0 \times 10^3$ | $3.0 \times 10^3$ | $3.0 \times 10^3$ |
| 72 hrs | <100 | <100 | <100 |

TABLE 5

Effect of sodium hyaluronate on *Pseudomonas aeruginosa*

| | Na-hyaluronate solutions | | |
|---|---|---|---|
| Time | 0.1% | 0.2% | 0.5% |
| | Test-organism /ml | | |
| 0 hr | $1.1 \times 10^7$ | $2.0 \times 10^7$ | $1.7 \times 10^7$ |
| 24 hrs | $1.0 \times 10^7$ | $2.0 \times 10^7$ | $1.5 \times 10^7$ |
| 48 hrs | $1.1 \times 10^6$ | $1.3 \times 10^6$ | $1.2 \times 10^6$ |
| 72 hrs | $1.2 \times 10^7$ | $1.1 \times 10^7$ | $1.2 \times 10^6$ |

From the results of Tables an advantageous picture appears: namely, that zinc hyaluronate solutions are obviously more effective than sodium hyaluronate solutions and the 0.1% zinc hyaluronate solution already exerts the same activity as 0.2% or 0.5% zinc hyaluronate solutions do. Based on this result an effective composition for external use can be developed.

The antibacterial effect of cobalt(II) hyaluronate was also investigated. The preparation of cobalt hyaluronate solution is described in Example 3.

EXAMPLE 3

Preparation of 0.1% Cobalt Hyaluronate Solution

After weighing 0.10 g of sodium hyaluronate of Example 1 in a 100 ml flask, 2.50 ml of cobalt chloride solution of 0.10 ml/liter concentration prepared with twice destined water (water for injection use, pyrogen-free, sterile) are added, then the volume is filled up to 50 ml with twice distilled water. It is allowed to swell overnight, then dissolved by shaking and finally, it is filled up with twice distilled water. After filtering the solution through a membrane filter of 0.45 $\mu$m pore size a cobalt hyaluronate solution of 0.10% concentration is obtained.

Fourth Series of Experiments

The microbiological investigations were carried out in the same way as described previously, except that *E. coli* bacteria were used instead of *Salmonella* sp. The results are summarized in Table 6.

TABLE 6

|  | *Staphylococcus aureus* Test-organism/ml | | *E coli* Test-organism/ml | |
| --- | --- | --- | --- | --- |
| Time | 0.1% Na-hy soln. | 0.1% Co-hy soln. | 0.1% Na-hy soln. | 0.1% Co-hy soln. |
| 0 hr | $3.0 \times 10^6$ | $1.9 \times 10^6$ | $4.5 \times 10^6$ | $5.8 \times 10^6$ |
| 4 hrs | $2.1 \times 10^6$ | $7.5 \times 10^5$ | $4.6 \times 10^6$ | $4.5 \times 10^6$ |
| 24 hrs | $1.3 \times 10^6$ | $3.5 \times 10^3$ | $1.8 \times 10^6$ | $1.0 \times 10^6$ |
| 48 hrs | $5.8 \times 10^4$ | $1.0 \times 10^2$ | $5.5 \times 10^5$ | $9.0 \times 10^2$ |
| 72 hrs | $2.8 \times 10^6$ | <10 | $5.5 \times 10^6$ | $1.0 \times 10^2$ |
| 96 hrs | $1.5 \times 10^6$ | <10 | $1.3 \times 10^6$ | <10 |
| 168 hrs | $1.6 \times 10^6$ | <10 | $2.5 \times 10^6$ | <10 |

It is clear from the above results of Table 6 that cobalt hyaluronate solution shows a similar activity as zinc hyaluronate solutions on both test organisms investigated whereas the comparative sodium hyaluronate solutions proved to be inactive also here when the deviations of the measuring methods are taken in account.

Fifth Series of Experiments

The antibacterial effect of zinc hyaluronate associate can be characterized by the following values of the minimum inhibitory concentration (MIC) and microbicidal concentration (CID) in comparison to the corresponding values of sodium hyaluronate.

MIC and CID values were determined by using solutions of 0.2% concentration. The determinations were conducted in a known way: a serial dilution was prepared from the substances to be tested and these solutions were artificially infected by the corresponding dilutions of the selected test organisms. After incubation at a suitable temperature for an appropriate time, the concentration series was visually evaluated and the minimum concentration was determined, which inhibited the growth of microorganisms (MIC value), or induced the death of the microorganisms (CID value). The results are summarized in Table 7.

TABLE 7

MIC and CID values of zinc hyaluronate ($\mu$g/ml)

|  | *Staphylococcus areus* | *Salmonella* | *Pseudomonas* | *Streptococcus* sp | *Escherichia coli* |
| --- | --- | --- | --- | --- | --- |
| MIC | 40 | 5.4 |  | 96 | 26 |
| CID | 120 | 160 |  | 400 | 310 |

The sodium hyaluronate solution of 0.2% did not exert an inhibitory effect on any of the test organisms even in a concentration of 2000 $\mu$g/ml therefore, the MIC values could not be determined.

It is obvious from the above Table 7 that MIC values of zinc hyaluronate indicate a considerable microbiological effect of the compound, which is by several orders better than that of sodium hyaluronate.

Sixth Series of Experiments

The possibility of a promising ophthalmological use of hyaluronic acid associates requires a good microbiological stability of compositions namely, their suitable resistance to the infection by various microorganisms. Extensive investigations were performed for the determination of microbiological stability of zinc and cobalt hyaluronate solutions in comparison to sodium hyaluronate usually employed in the ophthalmology. It has also been investigated if it were required to preserve the solutions containing zinc hyaluronate by using any preserving agent.

These examinations were carried out according to the article of USP XXII Edition (p. 1478) entitled "Antimicrobial preservatives effectiveness". The principle of this investigation is as follows. The substance to be tested was artificially infected by various test organisms and the change of count of the colony-forming units was observed as a function of time. Microbes registered in National Strain Collection of National Institute of Public Health (HNCMB) were employed as test organisms. The investigations were conducted with zinc and sodium hyaluronate solutions of various concentrations in the presence of or without a preserving agent.

The count of colony-forming units (number of germs) of the samples was determined by the plating (plate-moulding) method. The evaluation was performed by using an automated colony-counter at bacteria and fungi or visually respectively at moulds.

The results are shown in the Tables below. Each result means the average value of three parallel samples expressed in colony number/ml.

TABLE 8

Investigations on the microbiological stability of 0.1% zinc hyaluronate solution

| | Time of sampling | | | | | | | | | | |
|---|---|---|---|---|---|---|---|---|---|---|---|
| test organism | Start 0 hr | 1 day | 2 day | 3 day | 4 day | 5 day | 6 day | 7 day | 14 day | 21 day | 28 day |
| Staphylococcus aureus | $5.2 \times 10^5$ | $1.3 \times 10^4$ | $1.4 \times 10^3$ | $1.3 \times 10^3$ | $1.1 \times 10^3$ | $3.0 \times 10^2$ | <10 | <10 | <10 | 0 | 0 |
| Pseudomonas aeruginosa | $5.6 \times 10^5$ | 0 | 0 | 0 | 0 | 0 | 0 | 1 | 0 | <0 | 0 |
| Escherichia coli | $1.1 \times 10^5$ | $1.0 \times 10^4$ | $3.9 \times 10^3$ | $2.4 \times 10^3$ | $10^2$ | <100 | <100 | <100 | <10 | 0 | 0 |
| Aspergillus niger | $4.5 \times 10^5$ | $5.5 \times 10^4$ | $3.0 \times 10^4$ | $3.7 \times 10^3$ | $3.8 \times 10^3$ | $4.1 \times 10^3$ | $3.9 \times 10^3$ | $3.8 \times 10^3$ | $3.0 \times 10$ | $3.1 \times 10^3$ | $3.0 \times 10^3$ |
| Candida albicans | $6.4 \times 10^5$ | $2.5 \times 10^4$ | $4.2 \times 10^3$ | $2.5 \times 10^3$ | $2.1 \times 10^3$ | $2.6 \times 10^2$ | $3.1 \times 10^2$ | $3.2 \times 10^2$ | <100 | <10 | 0 |

TABLE 9

Investigations on the microbiological stability of 0.2% zinc hyaluronate solution

| | Time of sampling | | | | | | | | | | |
|---|---|---|---|---|---|---|---|---|---|---|---|
| test-organism | Start $0^{hr}$ | 1 day | 2 day | 3 day | 4 day | 5 day | 6 day | 7 day | 14 day | 21 day | 28 day |
| Staphylococcus aureus | $4.9 \times 10^5$ | $4.8 \times 10^4$ | $2.2 \times 10^3$ | <10 | <10 | <10 | <10 | 0 | <10 | 0 | 0 |
| Pseudomonas aeruginosa | $1.1 \times 10^5$ | 0 | 0 | 0 | 0 | 0 | 0 | 0 | 0 | 0 | 0 |
| Escherichia coli | $4.8 \times 10^5$ | $1.1 \times 10^5$ | $6.2 \times 10^4$ | $2.6 \times 10^4$ | $10^2$ | <10 | <10 | 30 | <10 | 0 | 0 |
| Aspergillus niger | $4.2 \times 10^5$ | $1.8 \times 10^4$ | $1.7 \times 10^4$ | $1.1 \times 10^4$ | $1.0 \times 10^4$ | $8.2 \times 10^3$ | $6.1 \times 10^3$ | $2.2 \times 10^3$ | $5.2 \times 10^2$ | $2.2 \times 10^2$ | $1.7 \times 10^2$ |
| Candida albicans | $3.9 \times 10^5$ | $1.1 \times 10^5$ | $1.9 \times 10^4$ | $2.0 \times 10^4$ | $1.8 \times 10^4$ | $6.1 \times 10^3$ | $3.5 \times 10^3$ | $3.1 \times 10^3$ | $9.8 \times 10^2$ | <100 | 0 |

TABLE 10

Investigations on the microbiological stability of 0.5% zinc hyaluronate solution

| | Time of sampling | | | | | | | | | | |
|---|---|---|---|---|---|---|---|---|---|---|---|
| test-organism | Start $0^{hr}$ | 1 day | 2 day | 3 day | 4 day | 5 day | 6 day | 7 day | 14 day | 21 day | 28 day |
| Staphylococcus aureus | $4.3 \times 10^5$ | $1.5 \times 10$ | $3.0 \times 10$ | <100 | 10 | <10 | 0 | 0 | 0 | 0 | 0 |
| Pseudomonas aeruginosa | $6.1 \times 10^5$ | 0 | 0 | 0 | 0 | 0 | 0 | 0 | 0 | 0 | 0 |
| Escherichia coli | $5.1 \times 10^5$ | $4.1 \times 10$ | $3.1 \times 10$ | $1.6 \times 10$ | <100 | 0 | 0 | 0 | 0 | 0 | 0 |
| Aspergillus niger | $4.8 \times 10^5$ | $4.2 \times 10$ | $3.6 \times 10$ | $2.8 \times 10$ | $2.8 \times 10^4$ | $2.4 \times 10^4$ | $4.0 \times 10^3$ | $3.6 \times 10^3$ | $3.1 \times 10^3$ | $1.9 \times 10^2$ | $1.8 \times 10^2$ |
| Candida albicans | $1.1 \times 10^5$ | $3.0 \times 10$ | $1.2 \times 10$ | $9.0 \times 10$ | $4.1 \times 10^3$ | $6.9 \times 10^2$ | $3.1 \times 10^2$ | $1.4 \times 10^2$ | 0 | 0 | 0 |

TABLE 11

Investigations on the microbiological stability of 0.5% zinc hyaluronate solution containing potassium sorbate

| | Time of sampling | | | | | | | | | | |
|---|---|---|---|---|---|---|---|---|---|---|---|
| test-organism | Start $0^{hr}$ | 1 day | 2 day | 3 day | 4 day | 5 day | 6 day | 7 day | 14 day | 21 day | 28 day |
| Staphylococcus aureus | $1.1 \times 10^5$ | $2.6 \times 10^3$ | 20 | <10 | 0 | 0 | 0 | 0 | 0 | 0 | 0 |
| Pseudomonas aeruginosa | $1.8 \times 10^5$ | 0 | 0 | 0 | 0 | 0 | 0 | 0 | 0 | 0 | 0 |
| Escherichia coli | $6.7 \times 10^5$ | $5.9 \times 10^4$ | $4.4 \times 10^3$ | $1.6 \times 10^2$ | <100 | 0 | 0 | 0 | 0 | 0 | 0 |

TABLE 11-continued

Investigations on the microbiological stability of 0.5% zinc hyaluronate solution containing potassium sorbate

| test-organism | Start $0^{hr}$ | 1 day | 2 day | 3 day | 4 day | 5 day | 6 day | 7 day | 14 day | 21 day | 28 day |
|---|---|---|---|---|---|---|---|---|---|---|---|
| Aspergillus niger | $4.6 \times 10^5$ | $4.1 \times 10^4$ | $1.8 \times 10^3$ | $2.1 \times 10^3$ | $1.9 \times 10^3$ | $1.6 \times 10^3$ | $1.6 \times 10^3$ | $5.4 \times 10^2$ | $2.0 \times 10^2$ | $1.9 \times 10^2$ | $1.6 \times 10^2$ |
| Candida albicans | $4.8 \times 10^5$ | $2.7 \times 10^4$ | $2.1 \times 10^3$ | $6.5 \times 10^3$ | $4.9 \times 10^3$ | $3.0 \times 10^3$ | $4.2 \times 10^2$ | $3.2 \times 10^2$ | 0 | 0 | 0 |

TABLE 12

Investigations on the microbiological stability of 0.5% sodium hyaluronate solution containing potassium sorbate

| test-organism | Start $0^{hr}$ | 1 day | 2 day | 3 day | 4 day | 5 day | 6 day | 7 day | 14 day | 21 day | 28 day |
|---|---|---|---|---|---|---|---|---|---|---|---|
| Staphylococcus aureus | $1.5 \times 10^5$ | $6.8 \times 10^4$ | $5.1 \times 10^4$ | $4.2 \times 10^3$ | $2.1 \times 10^3$ | $2.0 \times 10^2$ | 20 | <10 | <10 | 0 | 0 |
| Pseudomonas aeruginosa | $2.1 \times 10^5$ | $2.4 \times 10^4$ | $3.0 \times 10^3$ | <100 | <100 | 10 | 0 | 0 | 0 | 0 | 0 |
| Escherichia coli | $3.5 \times 10^5$ | $3.0 \times 10^4$ | $1.2 \times 10^4$ | $8.4 \times 10^3$ | $8.2 \times 10^3$ | $8.4 \times 10^3$ | $8.4 \times 10^3$ | $8.1 \times 10^3$ | $5.4 \times 10^2$ | $3.4 \times 10^2$ | 0 |
| Aspergillus niger | $3.2 \times 10^5$ | $5.4 \times 10^4$ | $3.2 \times 10^4$ | $6.8 \times 10^3$ | $5.4 \times 10^3$ | $5.5 \times 10^3$ | $4.8 \times 10^3$ | $5.1 \times 10^3$ | $4.7 \times 10^3$ | $3.0 \times 10^3$ | $2.8 \times 10^3$ |
| Candida albicans | $9.8 \times 10^4$ | $6.7 \times 10^4$ | $5.6 \times 10^4$ | $6.1 \times 10^4$ | $5.4 \times 10^4$ | $5.5 \times 10^4$ | $6.8 \times 10^4$ | $7.9 \times 10^4$ | $1.3 \times 10^5$ | $8.1 \times 10^4$ | $6.7 \times 10^4$ |

According to those described in USP XXII and the general requirements, a substance is suitably preserved if the count of bacteria introduced by artificial infection is reduced by 99% during 14 days; if test organisms do not propagate even during 14 days; as well as no temporary growth of any test organism is observed during 28 days of the investigation.

It can be seen from the results of investigation:
1. The microbiological stability of 0.1% zinc hyaluronate solution meets the regulations of USP XXII by considering that 4 organisms (Staphylococcus aureus, Pseudomonas aeruginosa, Escherichia coli, Candida albicans) from 5 microorganisms showed not only the required perishment but no living germ could be detected in the sample taken in the 28th day. The behavior of Aspergillus niger is regular and shows even a reduction by two orders.
2. The microbiological stability of 0.2% zinc hyaluronmate solution is similar to the stability of 0.1% zinc hyaluronate solution therefore, it meets the requirements of USP XXII.
3. The stability of 0.5% zinc hyaluronate solution meets the requirements of USP XXII according to the expectations; actually, the results indicate that the stability is improved by increasing the zinc hyaluronate concentration.
4. The stability properties of the solution containing 0.5% of zinc hyaluronate and 0.1% of potassium sorbate are sufficient but are not considerably (significantly) improved by the potassium sorbate preserving agent.
5. The 0.5% sodium hyaluronate solution containing 0.1% of potassium sorbate also meets the requirements of USP XXII in the cases of each microorganism tested.

From these results the very important conclusion can be drawn that no preserving agent is necessary for the zinc hyaluronate solution at all, in opposition to sodium hyaluronate showing even in the presence of the preserving agent a lower stability than that of zinc hyaluronate solution. A preserving agent is unconditionally necessitated for sodium hyaluronate solution since otherwise it becomes easily infected.

This recognition bears a great importance as preserving agents may frequently have an allergy-inducing effect therefore, their elimination makes the utilization of zinc hyaluronate very hopeful, especially in the ophthalmology.

Seventh Series of Experiments

The characterization of the microbiological stability of cobalt hyaluronate is shown in Table 13.

TABLE 13

Microbiological stability of 0.1 cobalt hyaluronate solution

| Test-organism | Day 0~30' | 24 hrs | 48 hrs | 72 hrs |
|---|---|---|---|---|
| Pseudomonas aeruginosa | $1.5 \times 10^4$ $6.5 \times 10^3$ | 0 | 0 | 0 |
| Salmonella sp. | $2.5 \times 10^4$ $4.8 \times 10^3$ | 0 | 0 | 0 |

It can be seen from the Table that the microbiological stability of 0.1% cobalt hyaluronate solution against Pseudomonas aeruginosa bacteria is similarly good as that of 0.1% zinc hyaluronate solution.

It can be observed that a nearly immediate effect occurs after inoculation. After termination of the 72 hours trial, a sterility examination was carried out with the result showing that the effect of cobalt hyaluronate on the bacteria tested is not static in its character but it is a bactericidal effect.

The preparation of ophthalmological and dermatological compositions, respectively for external use is described in the following Examples.

EXAMPLE 4

Preparation of 100 ml of Eye Drops Containing 0.1% of Zinc Hyaluronate

Sodium hyaluronate described in Example 1 was used for the preparation of eye drops.

After weighing 0.10 g of sodium hyaluronate of "purum pulvis" (pure powder) quality in a 100 ml flask, 1.87 ml of zinc chloride solution of 0.10 mol/liter concentration and 27.50 ml of sorbitol solution of 1.00 mol/liter concentration are added. (The solutions are prepared with twice distilled water.) Subsequently, the volume is filled up to 50 ml with twice distilled water. It is allowed to swell overnight, then dissolved by shaking and filled up to mark with twice distilled water. Finally, the solution is filtered off through a membrane filter (0.45 μm pore size).

EXAMPLE 5

Dermatological Composition Containing Zinc Hyaluronate

Preparation of 100 g of a Gel Containing 0.2% Zinc Hyaturonate

| | |
|---|---|
| Molecular weight: | 8000000 dalton |
| Protein content: | 0.094% |
| UV absorption: | 1% |
| A | : 0.320 |
| | 257 nm |
| | 1% |
| A | : 0.240 |
| | 280 nm |
| | C→O |
| Viscosity: | η = 14.5 dl/g |
| | 25 °C. |
| Hyaluronic acid content: | 95.2% |

After dissolving 0.2 g of sodium hyaluronate in about 30 ml of distilled water, 5.0 ml of 0.1 molar zinc chloride solution are added.

1.0 g of Carbopol 934 gelating (gel-forming) agent is mixed with 40 ml of distilled water, the stirring is continued for 1–1.5 hours, it is swollen for 10 to 12 hours and then 1.0 ml of 20% sodium hydroxide solution is added.

The zinc hyaluronate solution previously prepared is filtered through a filter of 0.45 μm pore size, poured to the gel under continuous stirring, then filled up to 100 g with distilled water.

The good results obtained on fungal and mould species of the stability investigations shown in Tables 8 to 12 indicate that zinc hyaluronate possesses not only an antibacterial but a significant antifungal effect, too.

Eighth Series of Experiments

The effectivity of the compounds on Helicobacter pylori bacteria also bears a similarly great importance. Based on this effect, the compounds are useful in the treatment or prevention of development of gastric and duodenal ulcers and mainly in the prevention of a re-infection after healing.

Study on the effectivity against Helicobacter pylori bacteria

These investigations were carried out by using 1.0 weight/vol. % zinc hyaluronate solution on Helicobacter pylori strains cultivated from the gastric is biopsy samples of patients suffering from various ulcers. An 1% solution of De-Nol (colloidal bismuth subcitrate) was used as reference substance. Agar culture medium (nutrient medium) supplemented with 10% of bovine blood was used for the investigations. Plates without compound to be tested were used as controls. The inoculated plates were incubated for 3 to 5 days at 37° C. in a gaseous environment containing 5% of oxygen and 7 to 8% of carbon dioxide. The value of minimum inhibitory concentration (MIC) was considered to be the minimum concentration of substances totally inhibiting the propagation of bacteria well-growing on the control plates. The MIC values of zinc hyaluronate and De-Nol, respectively measured on the strain tested are shown in Table 14.

TABLE 14

| Strain | zink-hyaluronate MIC μg/ml | De-Nol MIC μg/ml |
|---|---|---|
| 822/96 | 500 | 500 |

It is evident from the results shown in the Table that the in vitro activity of zinc hyaluronate on Helicobacter pylori is comparable to the activity of De-Nol used in the therapy. This fact is worth of consideration because De-Nol is a bismuth-containing composition having side effects (toxicity problems; in addition, its ingestion is unpleasant for the patient) cannot be neglected whereas likely, such side effects cannot be expected if zinc hyaluronate is used.

What is claimed is:

1. A method of treating a microbial infection in an eye of a patient in need of said treatment which comprises the step of topically administering to the eye of said patient a therapeutically effective amount of zinc hyaluronate or cobalt hyaluronate.

2. The method of treating a microbial infection defined in claim 1 wherein the microbial infection in the eye of the patient includes infection by *Staphylococcus aureus* and *Pseudomonas aeruginosa*.

3. A method of treating a patient having a gastric or duodenal ulcer induced by *Helicobacter pylori* bacteria which comprises the step of administering to said patient a therapeutically effective amount of zinc hyaluronate or cobalt hyaluronate.

4. A method of treating a patient with a healed gastric or duodenal ulcer induced by *Helicobacter pylori* bacteria for preventing reinfection with *Helicobacter pylori* bacteria which comprises the step of administering to said patient an amount of zinc hyaluronate or cobalt hyaluronate sufficient to prevent the reinfection.

* * * * *